(12) United States Patent
Barlow et al.

(10) Patent No.: US 12,064,253 B2
(45) Date of Patent: Aug. 20, 2024

(54) SWEAT MAPPING METHOD

(71) Applicant: Conopco, Inc., Englewood Cliffs, NJ (US)

(72) Inventors: Tammie Rose Barlow, Coventry (GB); Susan Bates, Heswall (GB); David Mark Haddleton, Kenilworth (GB); Ezat Khoshdel, Neston (GB); Gavin William Kirby, St. Neots (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 924 days.

(21) Appl. No.: 17/041,827

(22) PCT Filed: Feb. 27, 2019

(86) PCT No.: PCT/EP2019/054838
§ 371 (c)(1),
(2) Date: Sep. 25, 2020

(87) PCT Pub. No.: WO2019/185270
PCT Pub. Date: Oct. 3, 2019

(65) Prior Publication Data
US 2021/0007655 A1      Jan. 14, 2021

(30) Foreign Application Priority Data
Mar. 29, 2018 (EP) .................... 18164893

(51) Int. Cl.
*A61B 5/00* (2006.01)
*C08F 138/02* (2006.01)
(Continued)

(52) U.S. Cl.
CPC .......... *A61B 5/4266* (2013.01); *A61B 5/0071* (2013.01); *A61B 5/6801* (2013.01);
(Continued)

(58) Field of Classification Search
CPC ... A61B 5/4266; A61B 5/0071; A61B 5/6801; A61B 2562/164; A61B 5/0075;
(Continued)

(56) References Cited

U.S. PATENT DOCUMENTS

2004/0064087 A1    4/2004  Lastovich
2011/0059867 A1    3/2011  Kim et al.
(Continued)

FOREIGN PATENT DOCUMENTS

KR      101325912       11/2011
KR      20160052876     5/2016
(Continued)

OTHER PUBLICATIONS

IPRP1 in PCTEP2019054838; Sep. 29, 2020; World Intellectual Property Org. (WIPO).
(Continued)

*Primary Examiner* — Yi-Shan Yang
*Assistant Examiner* — Joseph A Tombers
(74) *Attorney, Agent, or Firm* — Stephanie Huang

(57) ABSTRACT

A method for mapping sweat production from the human skin, said method comprising the application of a polydiacetylene (PDA) prepared from a derivative of a conjugated diynoic acid having at least 18 carbon atoms, wherein the PDA changes colour when exposed to sweat, but does not change colour when exposed to pure water.

14 Claims, 2 Drawing Sheets

← Aromatic π-stacking of imidazolinium groups

← H-bonding between amide groups

← PDA chain

(51) Int. Cl.
*D21H 19/56* (2006.01)
*G01N 21/81* (2006.01)

(52) U.S. Cl.
CPC ............. *D21H 19/56* (2013.01); *G01N 21/81* (2013.01); *A61B 2562/164* (2013.01); *C08F 138/02* (2013.01)

(58) Field of Classification Search
CPC .... A61B 5/1032; A61B 5/6833; D21H 19/56; G01N 21/81; G01N 2021/7786; C08F 138/02; C09D 11/101; C09D 11/30; C09D 11/50
See application file for complete search history.

(56) References Cited

U.S. PATENT DOCUMENTS

| | | | |
|---|---|---|---|
| 2015/0329656 A1 | 11/2015 | Kim et al. | |
| 2016/0199581 A1 | 7/2016 | Cachemaille | |
| 2016/0235347 A1 | 8/2016 | Baig et al. | |
| 2018/0031486 A1 | 2/2018 | Lea | |
| 2018/0271416 A1 | 9/2018 | Begtrup | |
| 2018/0312708 A1* | 11/2018 | Kim | G06F 18/00 |

FOREIGN PATENT DOCUMENTS

| | | |
|---|---|---|
| KR | 101649547 | 8/2016 |
| WO | WO2009079156 | 6/2009 |
| WO | WO2014112829 | 7/2014 |
| WO | WO2015127249 | 8/2015 |
| WO | WO2016005987 | 1/2016 |
| WO | WO2017073926 | 5/2017 |

OTHER PUBLICATIONS

Salvo et al.; A Wearable Sensor for Measuring Sweat Rate; IEEE Sensors Journal; Oct. 2010; pp. 1557-1558; vol. 10 No. 10.
Joosub Lee et al.; Hydrochromic conjugated polymers for human sweat pore mapping; Nature Communications; Apr. 29, 2014; pp. 1-10; Macmillan Publishers Limited.
Seo et al.; Flexible patch-type hydrochromic polydiacetylene sensor for human sweat pore mapping; Journal of Applied Polymer Science; Aug. 26, 2016; pp. 1-8; Wiley Periodicals, Inc.
Hiroyuki Murota; Old and New Approaches for Assessing Sweating; Curr Probl Dermatol; 2016; pp. 22-29; vol. 51; S. Karger AG, Basel.
Bora Yoon et al.; An inkjet-printable microemulsion system for colorimetric polydiacetylene supramolecules on paper substratest; Journal of Materials Chemistry; Feb. 27, 2012; pp. 8680-8686; vol. 22; The Royal Society of Chemistry.
Search Report and Written Opinion in EP18164893; Sep. 27, 2018.
Dong-Hoon Park et al.; Inkjet-Printable Amphiphilic Polydiacetylene Precursor for Hydrochromic Imaging on Paper; Advanced Functional Materials; Jan. 1, 2016; pp. 498-506 (XP055380104); vol. 26, No. 4.
Search Report and Written Opinion in PCTEP2019054838; May 27, 2019.
Dong-Hoon Park et al.; Hydrochromic Approaches to Mapping Human Sweat Pores; Accounts of Chemical Research; May 9, 2016; pp. 1211-1222; vol. 49; American Chemical Society.
Search Report and Written Opinion in EP19212931; Jun. 2, 2020.

* cited by examiner

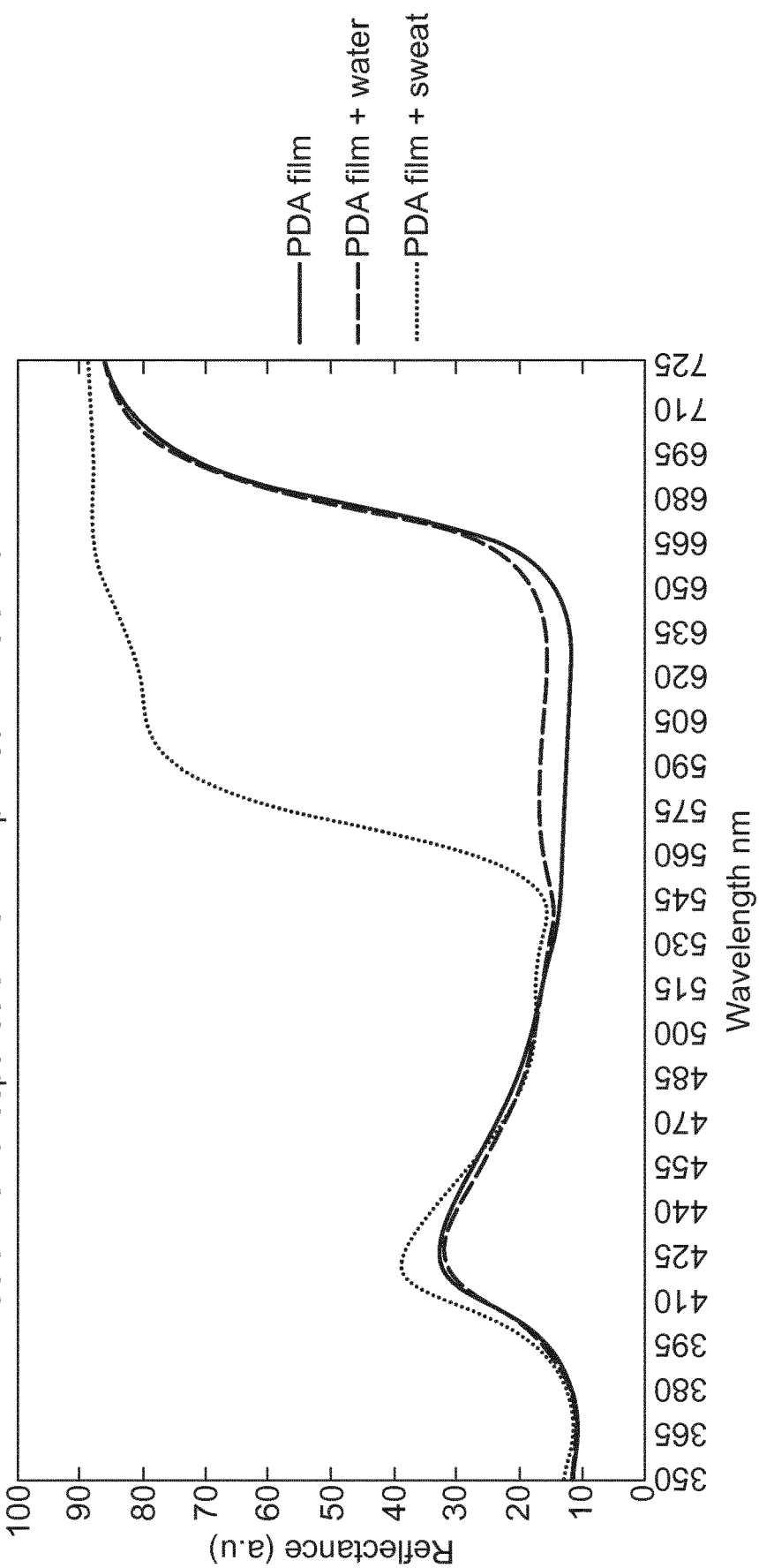

SWEAT MAPPING METHOD

RELATED APPLICATIONS

This application is a national phase filing under 35 USC 371 of International Application No. PCT/EP2019/054838, filed on Feb. 27, 2019, which claims priority from European Patent Application No. 18164893.2, filed Mar. 29, 2018, the contents of which are incorporated herein in their entirety for all purposes.

FIELD OF THE INVENTION

The present invention is in the field of detectors for sweat; in particular, sweat mapping and the quantification of sweat produced on various surfaces of the human body. It is also concerned with the assessment of antiperspirancy delivered by cosmetic compositions.

BACKGROUND

Numerous methods exist for the detection and quantification of sweat. In traditional clinical studies, panellists are required to sit in a hot room (for example, at 40° C. and 40% relative humidity) for a given period, prior to sweat being collected for a further period by cotton pads applied to the underarms. The pads are weighed before and after application to calculate the amount of sweat collected. Unfortunately, this method is not representative of sweating activity during normal daily activities and is not a good basis for evaluating the performance of an antiperspirant composition used during such activities. In addition, the method is inconvenient and uncomfortable for the panellists.

Numerous "Old and New Approaches for Assessing Sweating" are review by H. Murota in Curr. Probl. Dermatol., 51, 22-29, 2016.

A "Wearable sensor for measuring sweat rate" is described by P. Salvo et al in IEEE Sensors Journal, 10(10), 1557-1558, October 2010. The article describes a sweat-rate sensor integrated onto a textile, the sensor being a humidity capacitance sensor. This technology is more convenient for users than the gravimetric methods used in traditional clinical studies; however, there can be issues with the response and calibration of such sensors.

The present invention uses the colour change of a polydiacetylene (PDA) as in indicator of the presence of sweat and this sort of sensor technology has been used in other related applications.

PDA sensors have been used in flexible patch-type hydrochromic sensors for human sweat pore mapping on the hands and fingertips (Lee et al, *Nature Communications*, 5, 3736, 2014; http://dx.doi: 10.1038/ncomms4736 and Seo et al, *J. Appl. Polym. Sci.*, 44419, 2017; http://dx.doi: 10.1002/app.44419).

PDAs have been formulated into an inkjet-printable micro-emulsion system and applied to paper substrates (Yoon et al, *J. Mater Chem.*, 22, 8689, 2012 and Park et al, *Adv. Funct. Mater.*, 26, 498-506, 2016).

SUMMARY OF THE INVENTION

In a first aspect of the invention, there is provided a method for mapping sweat production from the human skin, said method comprising the topical application to the surface of the human of a polydiacetylene (PDA) prepared from a derivative of a conjugated diynoic acid having at least 18 carbon atoms, wherein the PDA changes colour when exposed to sweat, but does not change colour when exposed to pure water.

In a second aspect of the invention, there is provided the use of a method according to the first aspect of the invention to assess the relative performance of an antiperspirant active or formulation.

In a third aspect of the invention, there is provided a sweat mapping device comprising a flexible film with a polydiacetylene (PDA) applied to its surface, the PDA being of a derivative of a conjugated diynoic acid having at least 18 carbon atoms, wherein the PDA changes colour when exposed to sweat, but does not change colour when exposed to pure water.

In a fourth aspect of the invention, there is provided a method of manufacture of a sweat monitoring device, said method comprising steps of:

(i) preparing a derivative of a conjugated diynoic acid having at least 18 carbon atoms,
(ii) dissolving said derivative in a solvent and applying the resulting solution to the surface of a flexible film,
(iii) evaporating the solvent from the flexible film,
(iv) polymerising the derivative of the conjugated diynoic acid to give a polydiacetylene (PDA) upon the surface of the flexible film and, optionally,
(v) affixing the flexible film to the surface of a rigid support, such that the surface with the PDA upon it faces outwards, wherein the PDA changes colour when exposed to sweat, but does not change colour when exposed to pure water.

Herein, features expressed as "preferred" with regard to a particular aspect of the invention should be understood to be preferred with regard to each aspect of the invention (likewise, features expressed as "more preferred" or "most preferred").

Herein, preferred features of the invention are particularly preferred when used in combination with other preferred features.

BRIEF DESCRIPTION OF THE DRAWINGS

FIG. 2 illustrates the colorimetric response of the PDA-printed film to stimuli.

DETAILED DESCRIPTION OF THE INVENTION

Figure 1:
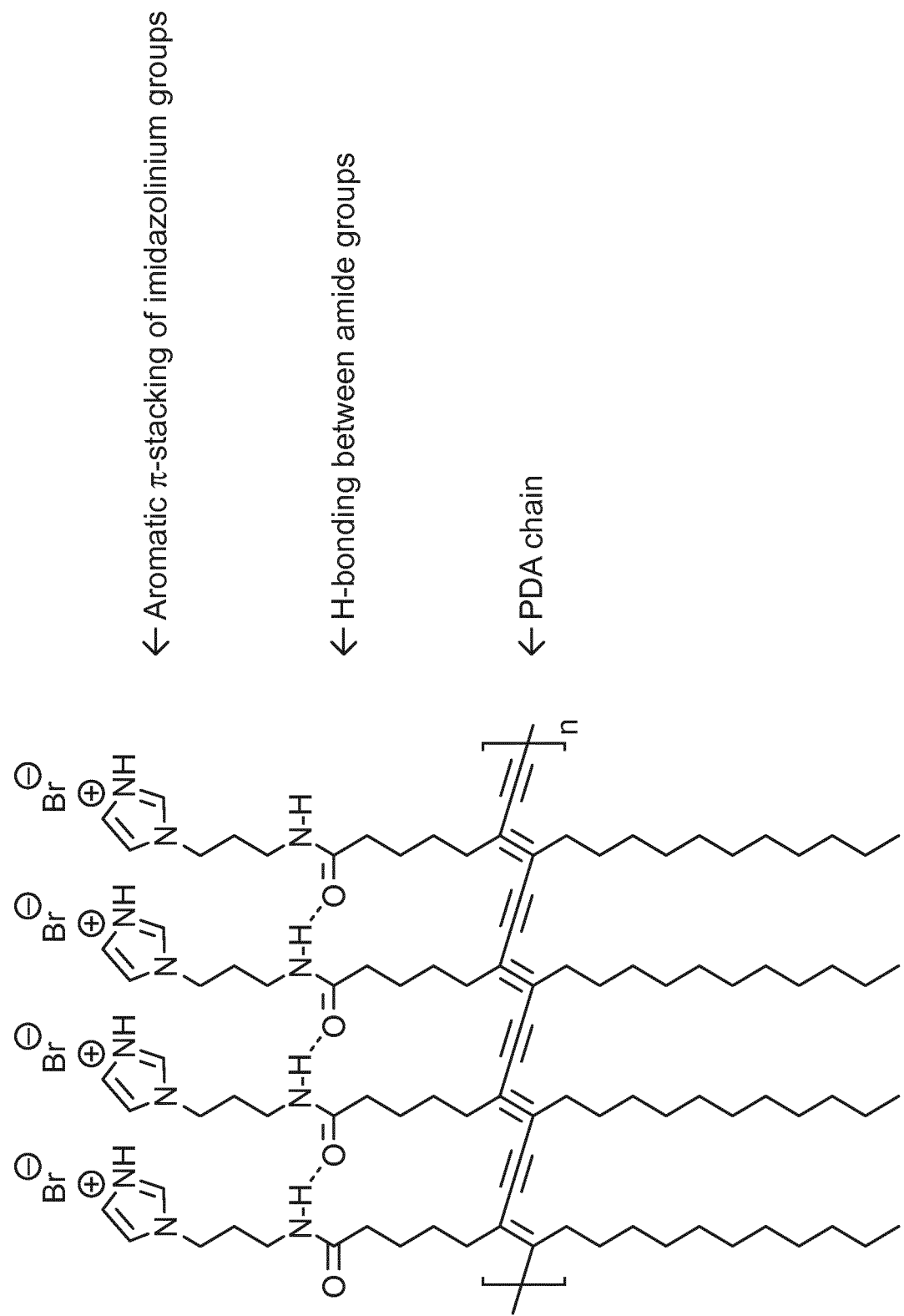
FIG. 1 illustrates an exemplary polydiacetylene (PDA).

Herein, the term "extended human torso" refers to the human torso plus arms and legs, but excluding the hands and feet.

Herein, the term "human torso" refers the trunk of the human body, excluding the limbs and the head, but including the axillae regions under the tops of arms.

Herein, the change in colour of a material may be as seen under visible and/or UV irradiation. When the colour change is under UV irradiation, this may alternative be termed as a change in fluorescence.

Herein, "Water sensitivity" refers the extent to which it a material changes colour on exposure to water; and especially changes in colour in the visible regions of the spectrum, i.e. under visible irradiation.

Herein, a "derivative" of a conjugated diynoic acid refers to a molecule possessing an additional organic radical, and not simply an ionised form of the acid, i.e. nota salt of the acid.

Herein, "ambient conditions" refers to 20° C. and 1 atmosphere pressure.

Herein, all amounts, ratios and percentages, should be understood to be by weight, unless otherwise indicated.

Herein, all amounts, ratios and percentages, should be understood to be optionally modified by the term "about", unless otherwise indicated.

Herein, the term comprising should be understood to mean 'including' but not necessarily 'consisting of' or 'composed of', i.e. it is used non-exhaustively.

The PDA is prepared from a derivative of a conjugated diynoic acid having at least 18 carbon atoms, i.e. it is formed from a polymerisation reaction of such a diynoic acid. The reaction is an addition polymerisation in which the conjugated diyne of the monomeric conjugated diynoic acid is transformed into a highly conjugated main chain structure with alternating double and triple bonds. The polymerisation reaction is typically induced by UV irradiation. The polymerisation reaction is typically a homopolymerisation.

It is the highly conjugated main chain structure with alternating double and triple bonds that lends the PDA its sensitivity to sweat, i.e. its ability to change colour when exposed to sweat.

The conjugated diynoic acids used in the present invention associate into what is sometimes called a supramolecular assembly. Such assemblies are characterised by relatively weak noncovalent interactions between molecules, for example hydrogen bonds. Whilst in this association, the diynoic acids may be polymerised, typically by the application of UV irradiation, to produce the PDA. The polymerisation forms covalent binds between the molecules, but the noncovalent interactions are usually retained. The resulting polymer may be termed a "polymeric supramolecule".

A preferred chain length for the conjugated diynoic acid prior to derivatisation is 20-25 carbon atoms and especially 25 carbon atoms. An especially preferred PDA is prepared from derivatisation and then polymerisation of 10,12-pentacosadiynoic acid (PCDA).

PDA's prepared from underivatized conjugated diynoic acids having at least 18 carbon atoms tend to have a high sensitivity to water, changing in colour when exposed to even quite low levels of water in a very short time period. This makes such "hydrochromic" polymers unsuitable for the application with which the present invention is concerned.

By using a derivative of a conjugated diynoic acid having at least 18 carbon atoms, wherein the PDA changes colour when exposed to sweat, but does not change colour when exposed to pure water, the present inventors have found that the resulting PDAS could be used in a method for mapping sweat production even in humid environments, such as the back or underarm regions of the human body.

A core aspect of the present invention is that by decreasing the water sensitivity of a PDA, the suitability of the PDA for quantifying the amount of sweat, a composition comprising water as its major constituent, on the surface of the human body, could be increased.

A key feature of the present invention is that the PDA does not change colour when exposed to pure water. Herein, this is defined by a lack of visible colour change when the PDA is in contact with a droplet of deionised water for a period of 20 seconds under ambient conditions. When this requirement is met, the PDA is said to have low sensitivity to water. PDA's having high sensitivity to water are unsuitable for use in the present invention.

A further key feature of the present invention is that the PDA visibly changes colour when exposed to sweat. Typically, there is an irreversible blue to red colour change within 1 to 10 seconds and preferably within 5 seconds of exposure to the sweat.

Without wishing to be bound by theory, it is hypothesised that PDAs suitable for use in the present invention change colour as a result of interaction with organic molecules present within the sweat.

A preferred PDA derivative is an amide. Such amides are produced when a conjugated diynoic acid Is reacted with an amine to form an amide before it is polymerised to give a "PDA-amide". PDA-amides are a preferred class of PDA derivatives for use in the invention.

Without wishing to be bound by theory, it hypothesised that the amide links in the PDA chains enable hydrogen-bonding between chains which thereby reduce the inter-chain mobility. This in turn reduces the water-sensitivity of the PDA making it more suitable for the present application. This H-boding between chains is illustrated for a particular PDA in FIG. 1.

Particularly preferred PDA-amides are basic in character as a result of having amine functionality remaining after the amidation reaction. Such "PDA-amidoamines" may optionally be used in their salt form, e.g. their hydrochloride or hydrobromide salt form.

Particularly preferred PDA-amidoamines have an imidazole "amine" substituent. Such "PDA-amido-imidazoles" and their salts, "PDA-amido-imidazolium salts", are especially preferred when they are amides of 10,12-pentacosadiynoic acid (PCDA).

Without wishing to be bound by theory, it hypothesised that the imidazole or imidazolium groups in the head group of the PDA enables aromatic Tr-stacking between head-groups which may reduce the mobility of the head groups. This may well reduce the water-sensitivity of the PDA making it more suitable for the present application. This Tr-stacking between head groups is illustrated for a particular PDA in FIG. 1.

We have found that the presence of unsubstituted imidazole or imidazolinium substituents on the PDA is particularly beneficial, especially when part of a PDA-amido-imidazole or PDA-amido-imidazolium salt. It is hypothesised that this may enhance the aromatic Tr-stacking described in the paragraph immediately above.

The most preferred PDA is a homopolymer of 3-(pentacosa-10,12-diynamido)propyl-imidazole or an imidazolium salt thereof, e.g. a hydrochloride or hydrobromide salt.

The PDA is "topically applied", i.e. it is applied to the surface of the human body. A preferred method of doing this is to first apply the PDA to the surface of a flexible film and then to apply to film, bearing the PDA, to the skin. In such embodiments, the film is typically applied such that the surface bearing the PDA contacts the skin.

Application of a PDA to a flexible film may adventurously be done by the following method.

In a first step, a solution of the monomer(s) from which the PDA is generated is prepared at a suitable concentration. The solvent is typically one that will dissolve the monomer(s) at a concentration of from 10 to 50% by weight at 20° C. and may be a solution in water, an organic solvent or a mixture of water and an organic solvent. A preferred solvent is a mixture of water and a water-miscible organic solvent. The concentration of the monomer(s) in the solution is preferably from 10 to 50%.

In a second step, the solution of monomers is applied to a flexible film. This may be done by brushing or spraying, for example. The substrate for the flexible film may be paper, fabric or synthetic polymer, is preferably paper. In preferred embodiments, the solution of the monomer(s) is applied to paper by Inkjet printing or by use of a flexo printer; in especially preferred embodiments, a reel-to-reel flexo printer is employed.

Following application, the solvent used to apply the monomer(s) is evaporated. This may preferably done under ambient conditions.

In a third step, the monomer(s) is/are polymerised on the flexible film to yield a PDA coated film. This is typically done using UV irradiation, optionally using equipment such a CL-1000 ultraviolet chamber.

The resulting layer of PDA on the flexible film is preferably a uniform layer of from 1 to 10 microns and more preferably a uniform layer of from 2 to 5 microns.

The term "uniform layer" means plus or minus 0.5 microns across the entirety of the PDA layer.

The resulting layer PDA on the flexible film is preferably from 0.2 to 0.8 mg/cm$^2$.

For application to the skin of the human body, the flexible film may be affixed to the surface of a rigid support, such that the surface of the flexible film with the PDA upon it faces outwards. The rigid support bearing the flexible film may then be pressed onto the skin.

Assessing the relative performance of an antiperspirant active involves an assessment of the extent of sweat production following treatment of the human skin with the antiperspirant active compared with the extent of sweat production following treatment with an alternative antiperspirant active or control.

Assessing the extent of sweat production is done in accordance with the first aspect of the invention. This may be done by assessing the extent of colour change of the applied PDA, which may advantageously be applied on a flexible film.

The extent of colour change may be expressed as the number of colour change 'dots' observed on the PDA, which corresponds to the 'number of sweat droplets' released by the sweat glands on the area of skin that the PDA has been within contact.

In some methods, the extent of colour change of the applied PDA may be expressed as the total extent of colour change of the PDA, expressed as a percentage of the area covered by the PDA, which would typically be applied on a flexible film in such methods. The 'percentage colour change' corresponds to the 'total coverage of sweat' of the area that was covered by the PDA.

EXAMPLES

N-Hydroxysuccinimide (0.048 g, 0.4 mmol., 0.1 equiv.), N-(3-dimethylaminopropyl)-N-ethylcarbodiimide hydrochloride (1.59 g, 4 mmol., 2 equiv.) and 1-(3-aminopropyl) imidazole (0.778 g, 6 mmol., 1.5 equiv.) were added to a solution of 10,12-pentacosadiynoic acid (1.55 g, 4 mmol., 1 equiv.) in anhydrous dichloromethane. After 18 hours HBr (48%) (2 equiv.) was added. The solution was concentrated under vacuum. The resulting residue was extracted with chloroform before being filtered and then concentrated under vacuum to yield 3-(pentacosa-10,12-diynamido)propyl-imidazolium bromide (PDCA-Im.HBr) as a white/pale yellow powder (2.2 g, 95%).

The PCDA-Im.HBr as prepared above was dissolved in a solution of water and 1-propanol (1:1) to give a 20% (w/w) solution. This solution was loaded into a blank printer cartridge and printed using an Epson WF-2010 printer, printing onto Navigator Ultra Smooth 120 g/m$^2$ paper using the print settings of plain paper and high-quality print. The printed patches were then allowed to dry fully before being cured for 24 seconds using a CL-1000 ultraviolet chamber (254 nm). The layer of PDA produced on the surface of the paper was 3 microns. The structure of the PDA is illustrated in FIG. 1.

The PDA-printed paper as described immediately above was affixed over a rigid support to produce a "sweat sensor" and was used to evaluate sweat in the underarm areas and back of the human body, as described below. The paper on the sweat sensor was found to undergo a blue to red colour change and bright fluorescence on contact with sweat. The paper on the sweat sensor did not undergo any colour change on contact with water. A fresh sheet of PDA-printed paper was used for each evaluation.

FIG. 2 illustrates the colorimetric response of the PDA-printed film to stimuli. The Figure shows the spectrum for the paper before exposure, after exposure to sweat and after exposure to water. The change in the spectra when the PDA-film is in contact with sweat is illustrative of a visible colour change from blue to red, whilst the lack of change when in contact with water is illustrative of the PDA-paper's lack of sensitivity to water.

The extent of colour change was assessed using a flatbed scanner and automated analysis. The extent of colour change was assessed either by use of a fluorescence microscope or using a flatbed scanner to generate mages of the sweat droplets. These images were subsequently analysed using an automated analysis algorithm. The extent of colour change induced by the contact with sweat can be assessed using various factors:

1. The number of sweat droplets identified by said colour change and/or fluorescence;
2. The area covered by the sweat droplets.

More conveniently the extent of the sweat can be expressed by:

3. The total area of the sensor covered by sweat—expressed as % sweat coverage.

Test 1

The method of the invention was used to assess the extent of underarm sweating in a clinical study. The aim of the study was to compare the sweat reduction efficacy of a standard antiperspirant roll-on product (comprising 12% aluminium chlorohydrate [ACH]) compared with a control composition (an ethanolic body spray comprising no antiperspirant active).

Thirty-six female subjects were required to not to use any antiperspirant product for 14 days prior to the study. The subjects attended the study site on three consecutive days for underarm washing and product application. The antiperspirant roll-on was applied to one underarm and the deo body spray to the other underarm—randomised. Subjects were requested not to wash their underarms or apply any other products to the underarms during the study. On Day 4, the subjects were required to sit in a hot room 40° C. and 40% relative humidity for 20 minutes. After the hot room sitting, the sweat sensor as described above was applied to the underarm regions of the panellists with a force of 400 g for 5 seconds to assess the extent of sweat in the axillae of the panellists. The PDA-printed paper of the surface of sensor was analysed to determine the % sweat coverage for each application.

The results from the study are shown in Table 1 below and in FIG. 2.

| | Treatment: | | | |
|---|---|---|---|---|
| | Control % sweat coverage | | Antiperspirant Roll-On % sweat coverage | |
| Day: | Mean | Std. Error | Mean | Std. Error |
| Day 1 | 52.11 | 5.69 | 28.33 | 5.32 |

The method of the invention showed clearly reduced sweat coverage following treatment with the antiperspirant roll-on.

Test 2

In further studies, the performance of a PDA prepared from an underivatized PDCA was assessed. The monomer selected for generation of the PDA was the caesium salt of 10,12-pentacosadiynoic acid, "PCDA-Cs", prepared according to the method of Lee et al, as disclosed in *Nature Communications*, 5, 3736, 2014; http://dx.doi: 10.1038/ncomms4736.

Studies with the PDCA-Cs prepared as described above proved problematic. First, it was found that solutions of the monomer tended to clog the inkjet printer making printing the monomer onto paper extremely difficult. Secondly, the PDA prepared by UV-initiated polymerisation of PDCA-Cs had very high water-sensitivity, making it unsuitable for use in the present invention.

Test 3

In further studies, the performance of a PDA prepared from a derivatized PDCA was assessed. The monomer selected for generation of the PDA was N-(3-(cyanomethyl)-1-(3-[pentacosa-10,12-diynamido]propyl)-1H-imidazol-3-ium bromide), "PDCA-CMIm", prepared according to the method of Park et al, as disclosed in *Adv. Funct. Mater.*, 26, 498-506, 2016).

Studies with the PDCA-CMIm prepared as described above proved problematic. Although solutions of the monomer had less issues with clogging of the inkjet printer than the solutions of PDCA-Cs, it was still found that the PDAS prepared by UV-initiated polymerisation of this monomer had high water-sensitivity, making it unsuitable for use in the present invention.

The invention claimed is:

1. A method for mapping sweat production from a human skin, comprising:
   applying to a surface of the human skin a polydiacetylene (PDA) prepared from a derivative of a conjugated diynoic acid having at least 18 carbon atoms;
   wherein the PDA is a homopolymer of 3-(pentacosa-10,12-diynamido)propyl-imidazole or a salt thereof;
   exposing the surface of the human skin to sweat; and
   mapping a colour change of the PDA; wherein, when exposed to pure water, the PDA does not change colour.

2. The method according to claim 1, wherein a fluorescence spectrum of the PDA changes when the PDA is exposed to the sweat.

3. The method according to claim 1, further comprising assessing a relative performance of an antiperspirant active or formulation, as compared to no antiperspirant, in sweat reduction.

4. The method according to claim 1, wherein the PDA is applied on a flexible film.

5. The method according to claim 4, wherein the PDA is on the flexible film as a uniform layer of from 2 to 5 microns.

6. The method according to claim 4, wherein the PDA is on the flexible film at a level of from 0.2 to 0.8 mg/cm$^2$.

7. A sweat mapping device comprising a flexible film with a polydiacetylene (PDA) prepared from a derivative of a conjugated diynoic acid having at least 18 carbon atoms, wherein the PDA is a homopolymer of 3-(pentacosa-10,12-diynamido)propyl-imidazole or a salt thereof, and further wherein the PDA-supramolecule is as recited in claim 1 and is applied to a surface of the flexible film.

8. A method of manufacture of a sweat monitoring device, the method comprising:
   (i) preparing a derivative of a conjugated diynoic acid having at least 18 carbon atoms,
   (ii) dissolving the derivative in a solvent and applying the resulting solution to a surface of a flexible film,
   (iii) evaporating the solvent from the flexible film,
   (iv) polymerising the derivative of the conjugated diynoic acid to give a polydiacetylene (PDA) upon the surface of the flexible film
   wherein the PDA is a homopolymer of 3-(pentacosa-10,12-diynamido)propyl-imidazole or a salt thereof.

9. The method according to claim 8, wherein the flexible film is affixed to a surface of a rigid support, such that the surface of the flexible film with the PDA faces outwards.

10. The method according to claim 8, wherein the solvent is a mixture of water and a water-miscible organic solvent.

11. The method according to claim 8, wherein the derivative of the conjugated diynoic acid is present in the solution at a concentration from 10 to 50% by weight.

12. The method according to claim 8, wherein the flexible film is a substrate composed of paper, fabric, or synthetic polymer substrate.

13. The method according to claim 12, wherein the substrate is paper.

14. The method according to claim 8, wherein the derivative of the conjugated diynoic acid is polymerised to give the PDA upon the surface of the flexible film by UV irradiation.

* * * * *